(12) United States Patent
Levine et al.

(10) Patent No.: US 6,183,454 B1
(45) Date of Patent: Feb. 6, 2001

(54) EXTERNALLY SUPPORTED FEMALE URINARY COLLECTOR

(76) Inventors: Laurence Levine, 189 E. Lake Shore Dr., #1E, Chicago, IL (US) 60611; Verne Anderson, 6218 N. Harlem Ave., Chicago, IL (US) 60631

( * ) Notice: Under 35 U.S.C. 154(b), the term of this patent shall be extended for 0 days.

(21) Appl. No.: 09/075,000

(22) Filed: May 8, 1998

(51) Int. Cl.[7] .............................. A61F 5/44; A61M 27/00; A61B 5/00
(52) U.S. Cl. .................. 604/329; 604/331; 604/355; 604/540; 604/544; 600/574; 4/144.3
(58) Field of Search ..................... 604/330, 327, 604/329–331, 349, 355, 351, 353, 544, 540; 4/144.3; 600/574

(56) References Cited

U.S. PATENT DOCUMENTS

| | | | |
|---|---|---|---|
| 3,432,864 | * 3/1969 | Schwartz | 4/144.2 |
| 3,432,865 | * 3/1969 | Schwartz | 4/144.2 |
| 4,202,058 | * 5/1980 | Anderson | 4/144.3 |
| 4,681,572 | * 7/1987 | Tokarz et al. | 604/329 |
| 4,713,066 | * 12/1987 | Komis | 604/353 |
| 4,846,817 | * 7/1989 | Mohr et al. | 604/329 |
| 4,886,508 | * 12/1989 | Washington | 604/327 |
| 4,889,532 | * 12/1989 | Metz et al. | 604/330 |
| 4,889,533 | * 12/1989 | Beecher | 604/330 |
| 5,370,637 | * 12/1994 | Brodeur | 604/329 |
| 5,549,584 | * 8/1996 | Gross | 604/355 |
| 5,827,248 | * 10/1998 | Crawford | 604/328 |

FOREIGN PATENT DOCUMENTS

| | | | |
|---|---|---|---|
| 0285585 | * 10/1988 | (EP) | 604/327 |
| 2126902 | * 4/1984 | (GB) | 604/330 |

* cited by examiner

Primary Examiner—Dennis Ruhl
(74) Attorney, Agent, or Firm—Hill & SImpson

(57) ABSTRACT

A urinary collection device for human females has a collecting basin with an oval inlet and a skirt around the outside of the oval inlet. A projection is provided from a short side of the oval inlet for insertion into the entrance to the vaginal opening to position the inlet about the urethral opening. A back of the collecting basin has a portion for receiving pressure to urge the inlet into a liquid tight seal against the user. The outlet of the collecting basin has a portion for connecting to a collecting tube which leads to a collecting reservoir. Some embodiments include a bellows between an outlet of the collecting basin and the portion for connection to the collecting tube. The bellows flexes to permit changes in angular orientation between the collecting basin and the collecting tube. An embodiment of the bellows may flex into a conical void within the back of the collecting basin to draw urine into the collection device upon unflexing, or expanding, of the bellows.

14 Claims, 6 Drawing Sheets

EXTERNALLY SUPPORTED FEMALE URINARY COLLECTOR

BACKGROUND OF THE INVENTION

1. Field of the Invention

The present invention relates generally to a collector for collecting urine from a human female, and specifically to an externally supported urine collector.

2. Description of the Related Art

Space travel provides exciting opportunities for women and men. However, the weightless environment provides particular problems for basic biological functions. Anatomical differences between women and men lead to a relatively easy solution to urination in a weightless environment for men but considerably greater challenges to provide for urination by females.

A solution to collecting urine from a human female in a weightless environment must be comfortable to use while ensuring no escape of urine. To date, absorbent pads have been used. These are not only uncomfortable but also impinge on the dignity of the user.

Medical circumstances may also prevent an individual from urinating in the customary way. For instance, individuals undergoing medical treatment or examination may be prevented from leaving a bed or examination table. A catheter is generally used in such circumstances for urination. The use of a catheter proves quite uncomfortable for the user. Lengthy recovery from an injury or illness or limited mobility due to handicap or aging may also prevent urination in the customary way. For such individuals, a catheter does not provide a long term solution. Instead, a bed pan or adult diaper may be used. Spills, leaks and hygiene then become issues.

A female urinary device has been proposed by Anderson and Levine, wherein a rigid opening attached to a urine collector tube is held in place about the urethra by a pair of flexible arms. The arms extend from one side of the rigid opening at an angle to the opening and at an angle to one another. The arms extend into the vaginal opening of the individual and the outward force exerted by the arms urges the opening into a sealing arrangement about the urethral opening. This device is designed for extended wear, however.

SUMMARY OF THE INVENTION

The present invention provides a urine collector for a human female which is used as needed for urination. The device may be used in a weightless environment, as well as other environments, without escape of urine.

The present urine collector has a collecting basin that is held in place about the urethral opening. An outer wall of the collecting basin tapers outwardly from an inlet opening of the basin and is free of sharp edges. A collecting tube is connected to an outlet of the collecting basin, the other end of the tube being connected to a collection bag or other reservoir. The inlet opening alignment with the urethral opening is assured by an intra-vaginal projection extending from a portion of the inlet opening of the collecting basin.

The collecting basin of the preferred embodiment has an elongated inlet opening of a generally oval shape. The intra-vaginal projection extends from one of the short sides of the elongated inlet. The intra-vaginal projection is generally the same width as the width of the inlet opening and may bulge slightly outward or taper gradually narrower. The free end of the intra-vaginal projection is rounded or hyperbolic.

To use, the intra-vaginal projection is introduced into the vaginal opening and the inlet of the collecting basin is pressed in place about the urethral opening. The device is held in place in this position by hand or by, for example, a belt. Preferably, an area is provided for gripping and for exerting the pressing force to hold the device in place during use. The outer wall of the collecting basin may extend to form a skirt to shield the fingers during use. The skirt also provides an extended edge-free surface to prevent discomfort for the user.

DETAILED DESCRIPTION OF THE PREFERRED EMBODIMENTS

Figures 1, 2, 3, 4, 5, 6:
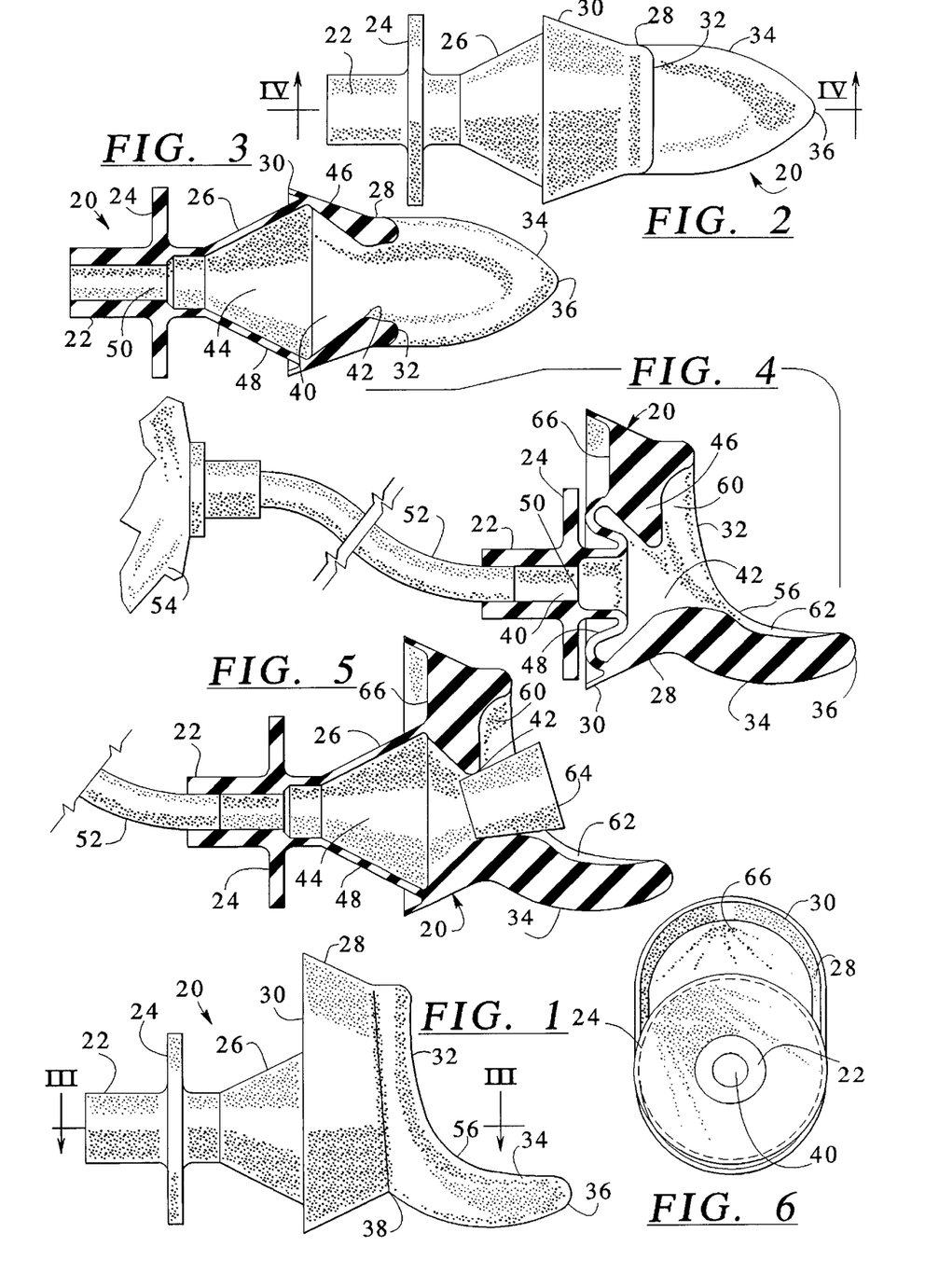
FIG. 1 is a side view of a preferred embodiment of the urine collector according to the principles of the invention.
FIG. 2 is a plan view of the preferred embodiment.
FIG. 3 is a cross-sectional view along line III—III of FIG. 1.
FIG. 4 is a cross-sectional view of the urine collector along line IV—IV of FIG. 2 and including a collecting tube and collecting reservoir.
FIG. 5 is a cross-sectional view of the urine collector similar to FIG. 4 and including a plug.
FIG. 6 is an end elevational view of the preferred urine collector.

Referring first to FIG. 1, a preferred urine collector 20 for use by a human female includes a collecting tube connection 22 attached to a pressure plate 24 on the other side of which is a bellows 26. The bellows 26 is connected to a collection basin body 28 about which is provided a skirt 30. The collecting basin body 28 has a body engaging face 32 from which extends an intra-vaginal projection 34.

The intra-vaginal projection 34 has a rounded narrow tip 36 at its end. From the end 36, the intra-vaginal projection 34 curves along a radius at its upper extent to the body engaging face 32, thereby forming a vestibule curve 56. The lower side of the intra-vaginal projection 34 also curves toward fourchette notch 38 between the skirt 30 and the intra-vaginal projection 34. When in position during use, the fourchette of the user rests in the fourchette notch 38 and the intra-vaginal projection 34 extends into the entrance of the vagina, resulting in the body engaging face 32 being in sealing engagement about the urethral opening of the user.

In FIG. 2, the intra-vaginal projection 34 widens gradually from the tip 36 to a width corresponding to the width of the basin body 28. The skirt 30 flares outward from the basin body 28, both in a lateral direction as seen in FIG. 2 and in a vertical direction as seen in FIG. 1. The flared skirt 30 and the gradually widening intra-vaginal projection 34 eases placement of the urine collector in position for use. The body engaging face 32 is rounded off as well for comfort and effective sealing engagement against the user's body.

Referring to FIG. 3, the urine collector provides a fluid passageway 40 from the body engaging face 32 to the collecting tube connection 22. At the body engaging face 32, the fluid passageway is of a width sufficient to ensure that the body engaging face is on either side of the urethral opening. The passageway narrows somewhat to an outlet 42 of the collecting basin 28 and then widens again in a bellows cavity 44 within the bellows 26. Thicker walls 46 enclose one end of the bellows cavity 44 while a thinner, more flexible membrane 48 encloses another end of the bellows cavity 44. The bellows cavity 44 is generally symmetrical relative to the flow direction of fluid through the fluid passageway 40. The fluid passageway 40 extends through the bellows 26, through a central opening 50 in the pressure plate 24 and to the collecting tube connection 22.

The thicker walls 46 at one side of the bellows and the thinner walls 48 at the other side of the bellows ensures that the collapse and expansion of the bellows is uniform each time it is collapsed. The thicker walls 46 provide a negative space into which the flexible walls 48 collapse. This also ensures that the fluid passageway, or lumen, 40 is uninterrupted when the bellows is in its collapsed position. The length of the tube between the pressure plate 24 and the downstream end of the bellows 44 is important to ensure complete collapse of the bellows.

FIG. 4 shows the present urine collector 20 ready for use. A collecting tube 52 is connected to the collecting tube connection 22 by insertion of the collecting tube 52 into the collecting tube connection 22. It is also possible to connect the tube 52 to the connection 22 by inserting the connection 22 into an appropriately dimensioned tube. Other means of providing a fluid tight connection are also possible and are considered within the scope of the present invention. It is also possible to form the connection 22 and the tube 52 in one piece. The tube 52 is connected at its other end to a reservoir 54, such as a collecting bag. Known collecting bags, or any other open or enclosed reservoir or containment vessel may be provided for receiving the urine collected by the present device.

After providing the tube 52 and reservoir 54, the device 20 is gripped by the fingers behind the skirt 30 and positioned for use by insertion of the projection 34 into the entrance of the vagina. The projection 34, the body engaging face 32, and the skirt 30 gently spread the tissues about the opening to the urethra. Pressure toward the urethral opening is exerted, preferably, by positioning the fingers behind the pressure plate 24 and pressing toward the body. This pressure collapses the bellows 26 as shown, with the thinner, more flexible membrane 48 folding into the bellows cavity 44 and against the thicker walls 46. The configuration of the bellows elements ensure a generally uniform collapse so that the central opening 50 in the pressure plate 24 is in registration with the outlet 42 of the collecting basin 28, thereby assuring continuity of the fluid passageway 40.

The device 20 is used in the position shown with the user voiding into the collecting basin 28 and the urine flowing through the fluid passageway 40, along the tube 52 and into the collecting bag 54. As can be seen in FIG. 4, the collecting basin 28 has a recess 60 extending from below a top of the body engaging face 32 to the outlet 42 of the collecting basin 28. A recess 62 is also provided in the intra-vaginal projection 34 from behind the tip 36 to the outlet 42. These recesses 60 and 62 function to basin the collected urine through the outlet 42 and accommodate variations of the position of the urethral opening from the vaginal opening for different users.

After completing voiding, the pressure on the pressure plate 24 is released, which permits the flexible membrane 48 of the bellows 26 to return to its non-collapsed position. This expansion of the bellows 26 draws any urine remaining in the recesses 60 and 62 and in the outlet 42 of the collecting basin 28 into the bellows 26. Spills are thereby avoided. Hygiene is improved by the prevention of spills. Furthermore, use in a weightless environment is possible, since the urine is drawn in under the force of air flow into the interior of the device precisely at the moment of release from the body. Gravity is not required to ensure containment of the urine.

FIG. 5 illustrates the position of the bellows 26 after expansion. The flexible membrane 48 has returned to the non-collapsed position, drawing air and any remaining urine into the interior of the bellows 26. FIG. 5 also illustrates use of a plug 64 fitted into the outlet 42 of the collecting basin 28 which keeps any urine in the device 20 or in the tube 52 from escaping. The user inserts the plug 64 into the outlet opening 42 upon completing use of the device 20. So that the plug 64 is handy when needed, it is preferably attached to the device 20 or to the tube 52 by a lanyard, cord or string.

It is also contemplated to provide a valve to prevent outflow of the collected urine, such a simple membrane valve at the outlet opening. A valve may be provided at the outflow side of the bellows 26 to prevent flowback of urine into the bellows 26 upon expansion of the bellows 26 from the non-collapsed position.

In the view of FIG. 6, the pressure plate 24 relative to the skirt 30 is shown. The pressure plate 24 of the illustrated embodiment is circular. The skirt 30 outlines the elongated or oval shape of the collecting basin 28. Since the fluid passageway 40 is offset from the center of the collecting basin 28, a back surface 66 is formed at the back side of the collecting basin 28 above the bellows 26. This back surface 66 may be contacted by the fingers during use as pressure is exerted toward the body for sealing engagement. The skirt 30 extends rearwardly from the back surface 66 to shield the fingers from contact with body tissues during use, as well as to shield the body tissues from contact with an edge of the back surface 66.

Figure 7:
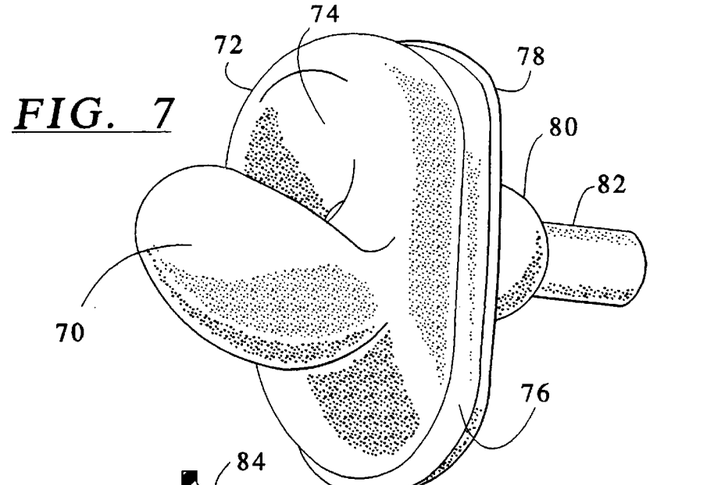
FIG. 7 is a perspective view of a second embodiment of the present urine collector.
Figure 8:
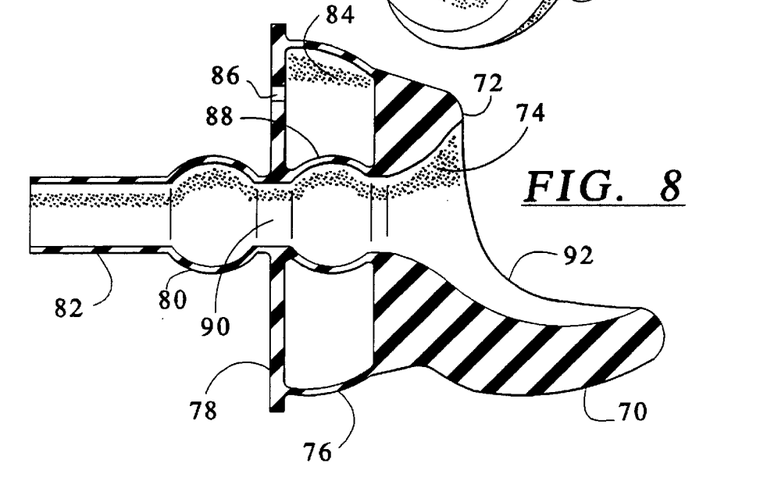
FIG. 8 is a vertical cross section of the second embodiment.
Figure 9:
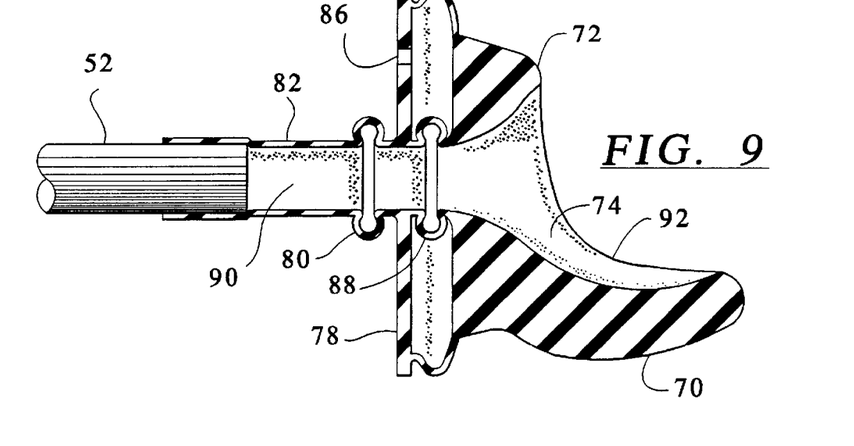
FIG. 9 is a vertical cross section similar to FIG. 8 showing the bellows in a compressed position.

FIGS. 7, 8 and 9 illustrate a second embodiment invention. In FIG. 7, an intra-vaginal projection 70 extends from a front of a body engaging surface 72 of a collecting basin 74. The outside of the collecting basin 74 extends to a skirt 76 which ends with a pressure plate 78. A flex bulb, or bellows, 80 is as the back side of the pressure plate 78, and a collecting tube connecting portion 82 is at the opposite side of the flex bulb 80. The intra-vaginal projection 70 and the collecting basin 74 are shaped similarly to the first embodiment, although variations in wall thicknesses and dimensions of parts are varied for comfort of a user. Since the skirt 76 is joined to the pressure plate 78, an air chamber 84 is formed at the back of the collecting basin 74. The illustrated embodiment is used by inserting the intra-vaginal projection 70 into the entrance of the vagina and pressing toward the body on the pressure plate 78, collapsing the air chamber 84. A vent opening 86 is provided to permit air to escape from the air chamber 84 during collapse of the air chamber.

A second bellows 88 is provided within the air chamber 84. This second bellows, or inner bellows, 88 forms a part of a fluid flow passageway 90 through the device. The second bellows 88 collapses as shown in FIG. 9 during compression of the pressure plate 78 toward the back of the collecting basin 74. The second bellows 88 prevents urine from collecting in the air chamber 84. Transition of the second bellows 88 from the collapsed to the non-collapsed state also draws in air and urine from the collecting basin 74 as in the first embodiment so that spillage is avoided.

The first bellows, or outer bellows, 80 permits the collecting tube 52 to move to angular orientations other than in line with the flow passageway 90 without kinking or otherwise blocking the flow passage 90 into the collecting tube 52. The tube 52 may be moved over a wide range of angles relative to the device as needed by the user without constriction of the flow path 90, since the flexible outer bellows 80 prevents kinking.

FIGS. 8 and 9 also illustrate the vestibule curve 92 which provides liquid-tight sealing engagement of the body engagement face 72 laterally of and below the urethral opening, or urethral meatus. The vestibule curve 92 may be varied depending on the anatomical differences of the user, but the shape illustrated herein has proven particularly leak-proof in tests by several different users.

Figure 10:
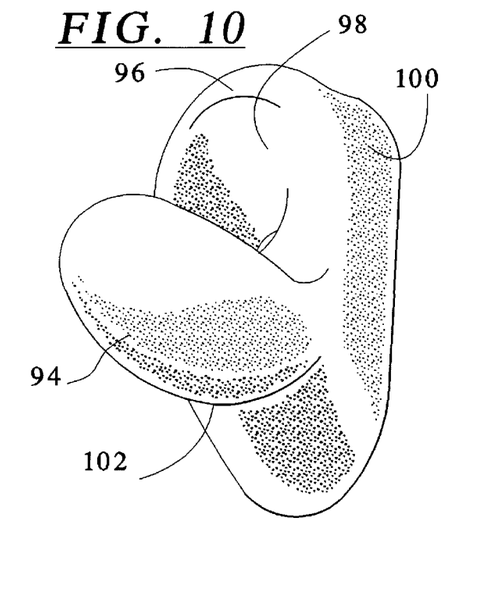
FIG. 10 is a perspective view of a third embodiment of a urine collector according to the invention.
Figure 11:
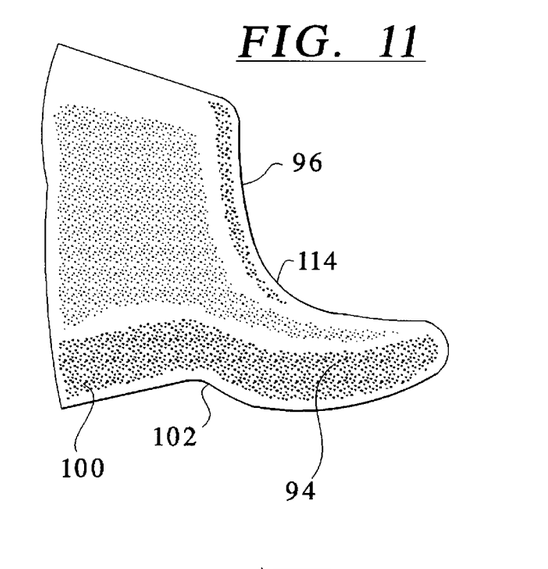
FIG. 11 is a side elevational view of the embodiment shown in FIG. 10.

FIG. 10 shows a third embodiment of the present urine collector, including an intra-vaginal projection 94 extending from a body engaging face 96 of a collecting basin 98. The outside of the collecting basin 98 is provided with a skirt 100 which defines a fourchette notch 102 at the underside of the intra-vaginal projection 94. The curved shape of the intra-vaginal projection 94 can be seen in the side view of FIG. 11. The skirt 100 extends rearward to a greater extent in this third embodiment than in the above described embodiments.

Figures 12, 13:
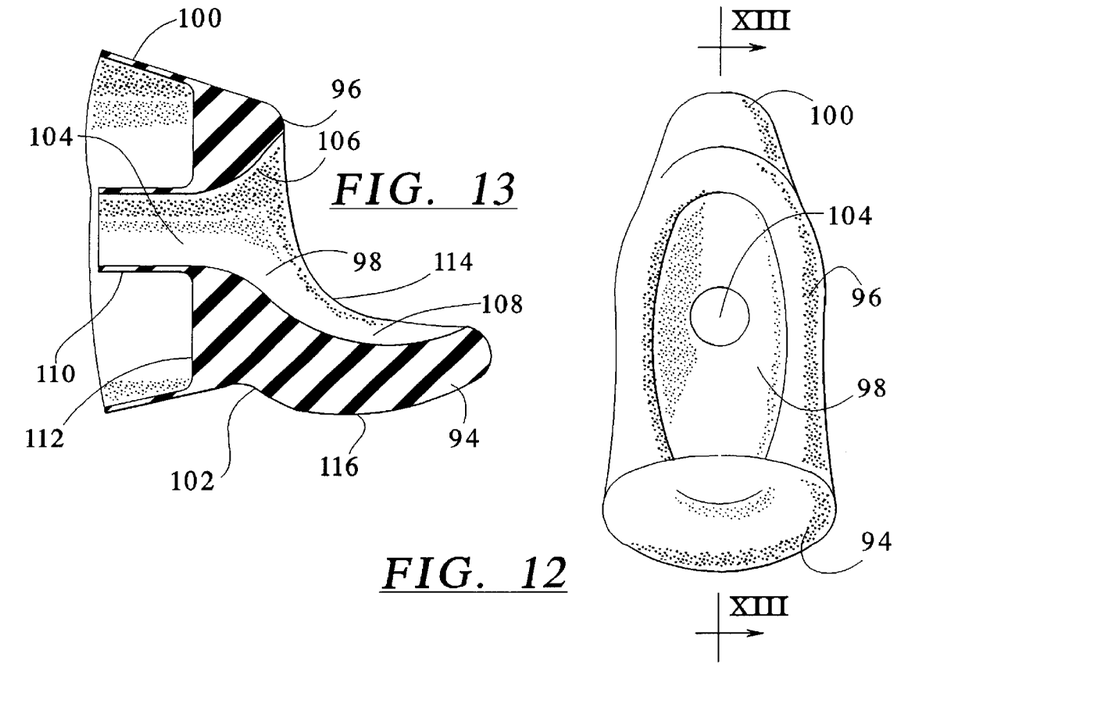
FIG. 12 is an end elevational view of the third embodiment.
FIG. 13 is a cross-sectional view along line XIII—XIII of FIG. 12.

In FIG. 12 is seen the elongated, generally elliptical shape of the collecting basin 98. An outlet 104 of the collecting basin 98 is positioned higher in the collecting basin 98 near a center of the elliptical shape. The shape of the collecting basin 98 and the position of the outlet 104 is a matter of personal preference for the user, depending on which arrangement works best.

With reference to FIG. 13, the collecting basin 98 has the upper recess 106 below the upper part of the body engaging face 96 and a lower recess 108 in the intra-vaginal projection 94 leading to the outlet 104. The outlet 104 leads to a collecting tube connection 110 to which is connected a collecting tube 52 and reservoir 54 (as shown in FIG. 4). A back surface 112 lies around the collecting tube connection 110 at the back of the collecting basin 98. The skirt 100 extends beyond the back surface 112 for a significantly greater distance than in the first embodiment. This embodiment lacks the bellows of the first two embodiments but does include a vestibule curve 114 from the intra-vaginal projection to the body engaging face 96. This vestibule curve 114 in combination with the fourchette notch 102 and an intra-vaginal curve 116 at the underside of the intra-vaginal projection ensure that the proper position of the device is achieved quickly and is maintained during voiding.

A user positions the user's fingers on the back surface 112, such as above and below the collecting tube connection 110 to grip the device. The device is moved into position with the intra-vaginal projection 94 extending into the vaginal entrance and pressure is exerted on the back surface 112 by the user's fingers to press the body engaging face 96 into sealing engagement about the opening of the urethra. The device is then held in this position during voiding. The user's fingers are kept clean by the skirt 100 extending about the back surface 112. A plug may be used to close the outlet 104 after use if desired.

References to a user and the user's fingers include not only the individual whose urine is being collected by the present device and who may use the device alone, but also include a care giver or medical personnel who may be assisting the individual in positioning and holding the present device.

Figure 14:
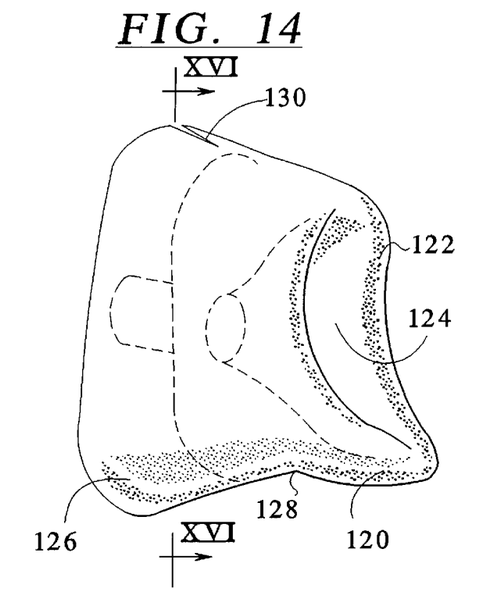
FIG. 14 is a perspective view of a fourth embodiment of the urine collector of the invention.

FIG. 14 illustrates yet a further embodiment. This fourth embodiment has an intra-vaginal projection 120 extending from a body engaging face 122 of a collecting basin 124. A skirt 126 extends rearwardly from the outside of the collecting basin 124. The intra-vaginal projection 120 extends forward to a lesser extent than in previous embodiments, depending on the needs and comfort of the user. A fourchette notch is provided for proper positioning but in this embodiment it is shallower. The skirt 126 extends rearward to a relatively great extent and a slit 130 is provided at the top of the skirt 126 as a clearance of the user's fingers.

Figure 15:
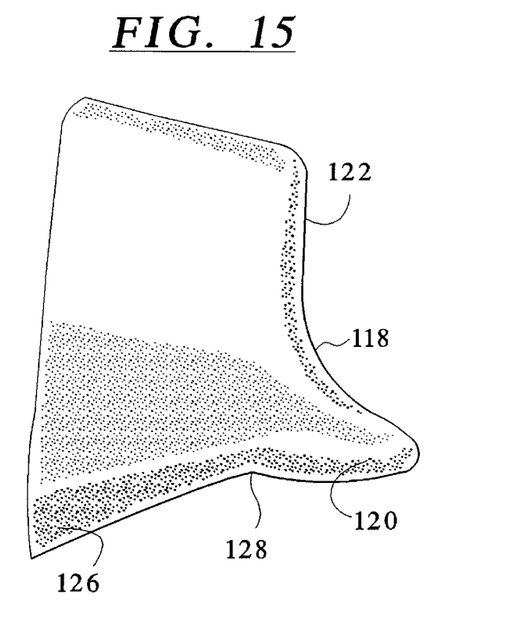
FIG. 15 is a side elevational view of the fourth embodiment of FIG. 14.

The less pronounced extension of the intra-vaginal projection 120 is particularly apparent from the view of FIG. 15. The skirt 126 extends downward to a greater extent than previous embodiments, as well. The upper surface of the intra-vaginal projection is formed into a vestibule curve 118 to prevent leakage.

Figures 16, 17:
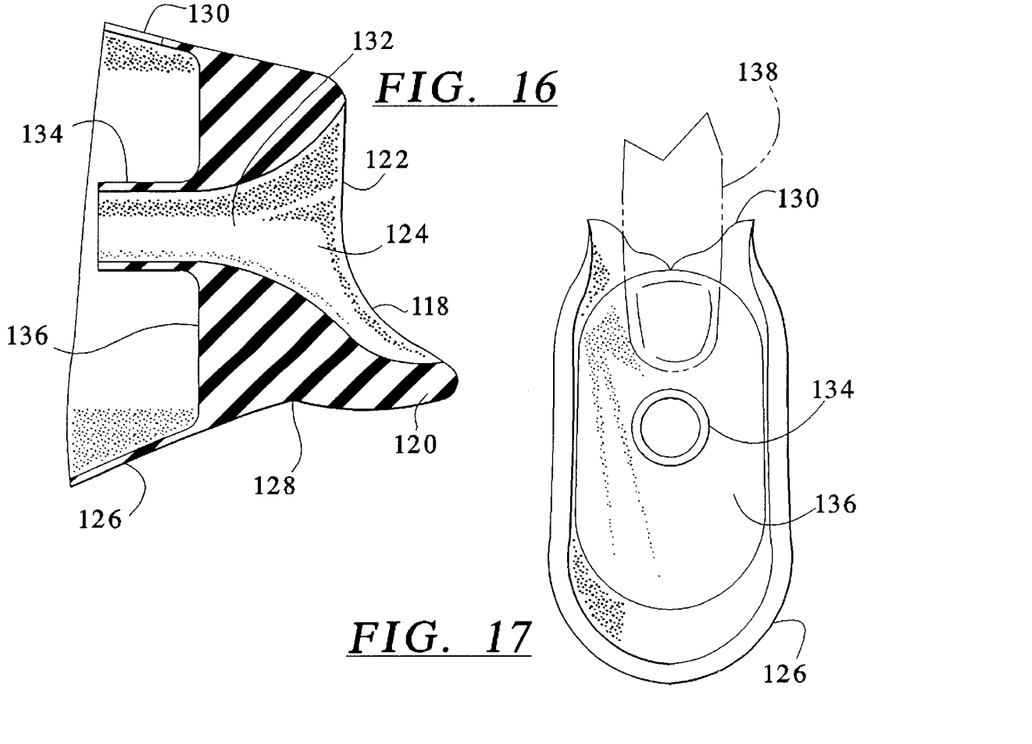
FIG. 16 is a cross-sectional view along line XVI—XVI of FIG. 14.
FIG. 17 is an end view of the fourth embodiment showing manual holding of the urine collector in place.

In FIG. 16, the collecting basin 124 has steeper angled walls leading to an outlet 132. The outlet 132 leads to the collecting tube connection 134 to which is connected the collecting tube 52 and reservoir 54. A back surface 136 of the collecting basin 124 receives pressure from the user's fingers to hold the device in position.

FIG. 17 shows a user's finger 138 pressing against the back surface 136 to hold the device during use. The user's finger 138 flexes the skirt 126 at the slit 130, which opens to provide clearance for the finger 138.

Figure 18:
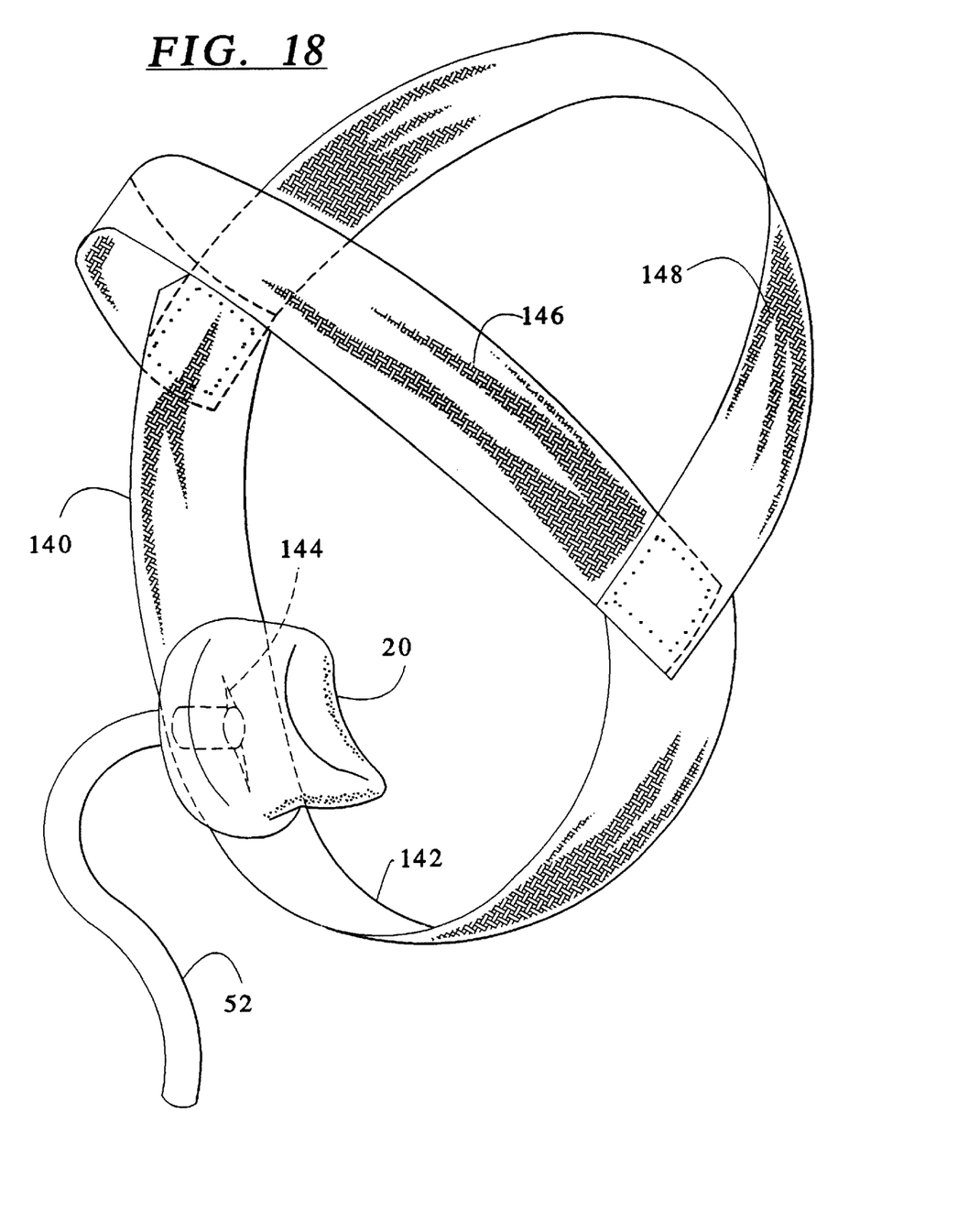
FIG. 18 is a perspective view of a belt for holding the present urine collector in place.

In FIG. 18 is shown an alternative to holding the device by the user's fingers, namely a belt 140. The belt 140 includes a lower strap 142 with an opening 144 through which extends the collecting tube 52 or the collecting tube connection. The urine collector device 20 is on the inside of the lower loop 142. Side loops 146 and 148 are connected to the lower loop 142 and extend about the user's hips during use. The belt 140 permits the present urine collector to be held without using the hands and permits extended wear of the device.

Figures 19, 20:
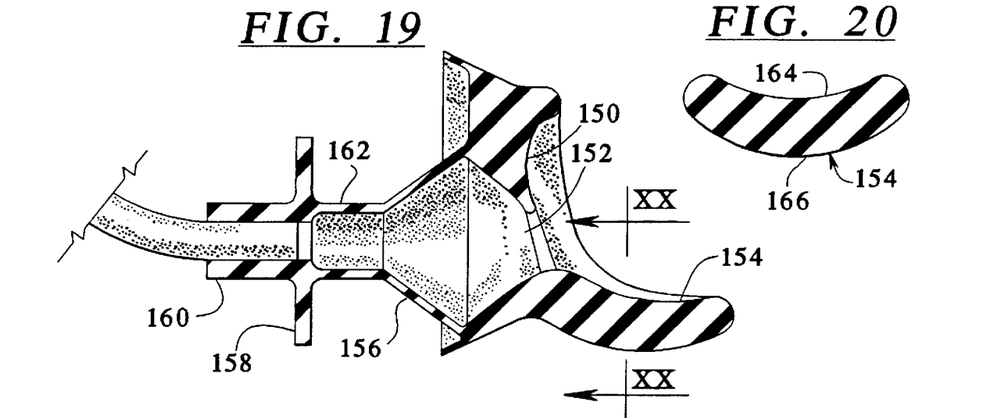
FIG. 19 is a side cross-sectional view of a further embodiment.
FIG. 20 is a cross section along line XX—XX of FIG. 19.

In FIG. 19 is shown an embodiment of the present collector which has a collecting basin 150 with a collecting opening 152 of a predetermined diameter. The collector also has an intra-vaginal projection 154, a bellows 156, a pressure plate 158 and a collecting tube connection 160 as in the first described embodiment. The bellows 158 has an enlarged throat 162 that is of the same diameter as the collecting opening 152.

FIG. 20 shows a cross section of the intra-vaginal projection 154. An upper surface 164 thereof is curved in a shallow depression which accommodates the tissues in this region and so avoids discomfort to the user as well as prevents compression of the urethra. A lower surface 166 is also curved, generally about the same center as the curve of the upper surface 164. The lateral edges 168 are rounded off, also for comfort.

Figure 21:
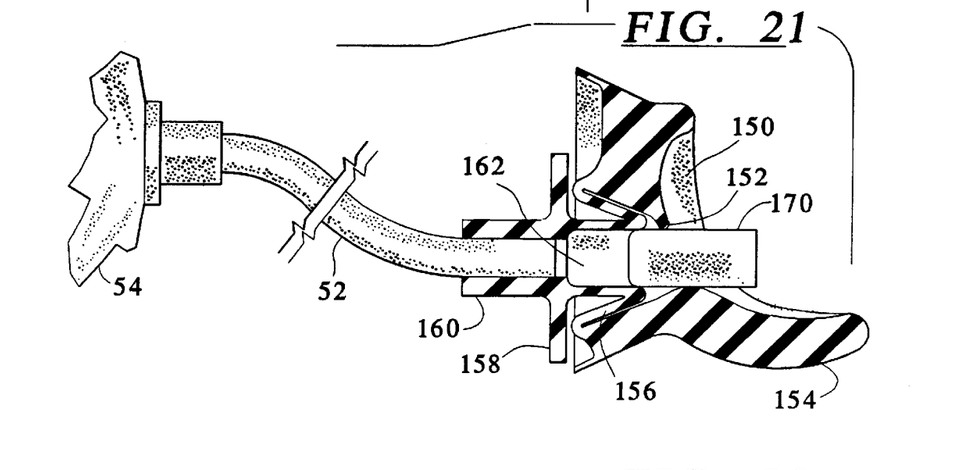
FIG. 21 is a cross section of the embodiment of FIG. 19 showing a plug in the collecting opening.

Referring to FIG. 21, the device of FIG. 19 is shown after having been used. The user releases the pressure from the pressure plate 158, permitting the bellows 156 to expand and draw in any fluids that may remain in the area of the collecting basin 150. The fluids are retained in the bellows 156 by applying a plug 170 into the opening 152. The bellows 156 is then compressed to the position shown in FIG. 21. The presence of the plug 170 prevents the fluids from exiting the device through the opening and forces the fluids into the collecting tube 52 and the collecting bag 54. The compression of the bellows 156 expels nearly all the fluids, in particular urine, from the bellows 156.

Figure 22:
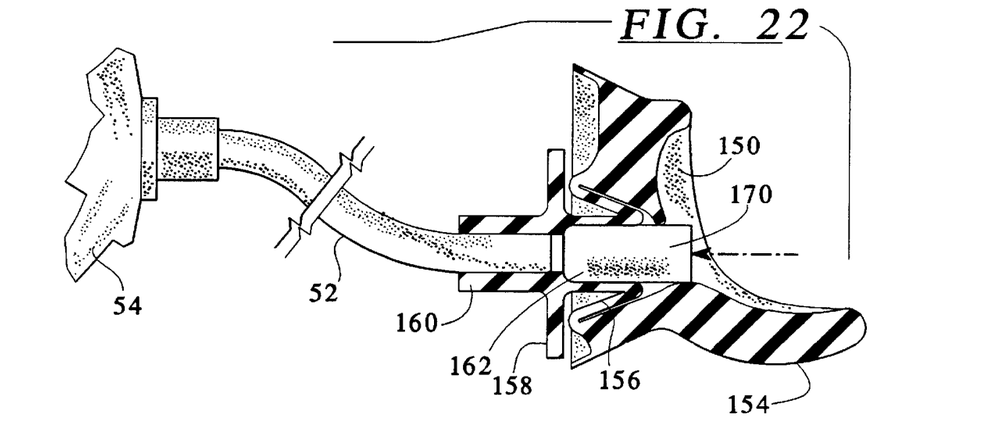
FIG. 22 is a cross section of the embodiment of FIG. 19 showing the plug inserted into the bellows channel.

The plug 170 is then pressed in further to fit into the throat 162 at the downstream end of the bellows 156. The movement of the plug 170 into the throat 162 forces the fluids down into the collecting tube 52, preventing any quantity of urine from remaining in the device. The plug 170 forms an air-tight and liquid-tight seal against the opening 152 and against the walls of the throat 162 to that the bellows 156 is prevented by vacuum pressure from expanding. The present collecting device thus ensures that fluids are forced into the collecting tube 52 and the collecting bag 54 to the greatest extent possible, rather than remaining in the collecting device.

The use of the plug 170 as described above is useful to prevent leakage of urine from the collector in ordinary circumstances. It becomes even more important in a weightless environment since gravity cannot be counted on to cause the urine to flow into the outlet of the collecting basin and down the tube into the bag or reservoir.

The present device is formed of flexible elastomeric material, such a silane compound. The device may instead be made of SBS or of a compound of materials, such a styrene for the rigid parts such as the collecting basin and SBS for the flexible parts such as the bellows. The device is formed by injection molding, compression molding, or other molding techniques. Preferably, it is a single piece molded in one piece or as several parts and then joined together to provide a single piece device.

In one manufacturing process, the device is made in two pieces (the collector basin piece and the bellows, pressure plate piece) that are then bonded together. The formation of the pieces is by injection molding, dies, or by side-draw molding. It is also contemplated to mold the device in three pieces (the collector basin piece, the bellows piece, and the pressure plate piece) to simplify the molding process and reduce the costs of the molds.

Although other modifications and changes may be suggested by those skilled in the art, it is the intention of the inventors to embody within the patent warranted hereon all changes and modifications as reasonably and properly come within the scope of their contribution to the art.

We claim:

1. A urinary collector for a human female, comprising:
   a collecting basin having an inlet opening and an outlet opening, said inlet opening having a rounded edge;
   a collecting tube connecting portion for connection to a collecting tube, said collecting tube connecting portion being in fluid communication with said outlet opening of said collecting basin; and
   structure defining a collapsible chamber between said outlet opening of said collecting basin and said collecting tube connecting portion, said structure having a thick walled side and a thin walled side, said thin walled side having a predetermined shape in a non-collapsed condition, said thin walled side collapsing into said thick walled side upon axial compression by folding of said predetermined shape to collapse said collapsible chamber, said thick walled side being of sufficient thickness to retain its shape when subjected to the axial compression during collapse of said thin walled side.

2. A urinary collector as claimed in claim 1, further comprising:
   a grip plate extending transversely from said collecting tube connection portion so that pressure on said grip plate in a direction opposite fluid flow collapses said collapsible chamber.

3. A urinary collector as claimed in claim 1, further comprising:
   a tapered outer wall extending from said inlet opening and being an exterior surface of said collecting basin;
   an intra-vaginal projection extending from said inlet opening at a short edge of said inlet opening, said intra-vaginal projection ending in a smoothly curved projecting end, and having a rounded edge along its perimeter, said rounded edge of said intra-vaginal projection joining said rounded edge of said collecting basin at a gradually curving fourchette notch, said intra-vaginal projection including an elongated concavity contiguous with an interior of said collecting basin, said elongated concavity being within said rounded edge of said intra-vaginal projection;
   wherein said tapered outer wall joins an outside of said intra-vaginal projection at an angle defining said fourchette notch.

4. A urinary collector as claimed in claim 1, further comprising:
   a belt forming a circle for encircling a user's waist;
   a strap extending between opposite sides of said belt;
   a means for engaging said collecting tube connecting portion on said strap.

5. A urinary collector as claimed in claim 1, wherein said thick walled side is formed by a body of said collecting basin.

6. A urinary collector for a human female, comprising:
   a collecting basin having an inlet opening and an outlet opening, said inlet opening having a rounded edge, said inlet opening defining a forward end of said urinary collector;
   a tapered outer wall extending from said inlet opening and being an exterior surface of said collecting basin;
   a collecting tube connecting portion for connection to a collecting tube, said collecting tube connecting portion being in fluid communication with said outlet opening of said collecting basin and extending in a rearward direction relative to said forward end; and a flexible skirt extending from said tapered outer wall in a generally rearward direction relative to said forward end.

7. A urinary collector as claimed in claim 6, further comprising:

a gripping space within a rearwardly directed portion of said flexible skirt.

8. A method for collecting urine from a human female, comprising the steps of:

positioning an inlet of a collecting basin about a urethral opening of the human female;

compressing a bellows on the collecting basin prior to urination by the human female;

releasing compression force on said bellows to permit said bellows to expand to draw any remaining urine into said bellows; and inserting a plug into an outlet of said collecting basin.

9. A method as claimed in claim 8, further comprising the steps of:

compressing said bellows while said plug is in said outlet of said collecting basin; and inserting said plug into a throat at a downstream side of said bellows relative to a fluid flow direction during urine collection.

10. A urinary collector for a human female, comprising:

a collecting basin having an inlet opening and an outlet opening said inlet opening having a rounded edge;

a collecting tube connecting portion for connection to a collecting tube said collecting tube connecting portion being in fluid communication with said outlet opening of said collecting basin;

first and second compressible bellows in a fluid flow path between said outlet of said collecting basin and said collecting tube connecting portion;

a tapered outer wall extending from said inlet opening and being an exterior surface of said collecting basin;

a skirt extending from said tapered outer wall;

a cap plate closing an end of said skirt opposite said tapered outer wall, said skirt and said cap plate enclosing said first compressible bellows, one of said cap plate and said skirt defining a vent opening.

11. A urinary collector for a human female, comprising:

a collecting basin having an inlet opening and an outlet opening, said inlet opening having a rounded edge;

a collecting tube connecting portion for connection to a collecting tube, said collecting tube connecting portion being in fluid communication with said outlet opening of said collecting basin;

a tube connected to the collecting tube connecting portion;

a plug for selective insertion in said outlet opening of said collecting basin while said tube is connected to the collecting tube connecting portion.

12. A urinary collector for a human female, comprising:

a collecting basin having an inlet opening and an outlet opening, said inlet opening having a rounded edge;

a collecting tube connecting portion for connection to a collecting tube, said collecting tube connecting portion being in fluid communication with said outlet opening of said collecting basin;

a generally rigid wall defining an interior space in communication with said outlet opening of said collecting basin, said interior space being a diaphragm receiving space;

a flexible diaphragm mounted to selectively flex into said diaphragm receiving space, said flexible diaphragm connected to said collecting tube connecting portion, said interior space being a fluid passageway between said outlet opening of said collecting basin and said collecting tube connecting portion, said flexible diaphragm folding into said diaphragm receiving space upon receiving compression force along a direction of fluid movement to substantially reduce a volume of said interior space.

13. A urinary collector for a human female, comprising:

a collecting basin having an inlet opening and an outlet opening, said inlet opening having a rounded edge;

a collecting tube connecting portion for connection to a collecting tube, said collecting tube connecting portion being in fluid communication with said outlet opening of said collecting basin;

a collapsible chamber between said outlet opening of said collecting basin and said collecting tube connecting portion, said collapsible chamber having a thick walled side and a thin walled side, said thin walled side having a predetermined shape in a non-collapsed condition, said thin walled side collapsing into said thick walled side upon axial compression by folding of said predetermined shape to collapse said collapsible chamber, and a narrow throat dividing said collecting basin from said collapsible chamber through which air is drawn upon expansion of said collapsible chamber by release of the axial compression.

14. A method for collecting urine from a human female, comprising the steps of:

compressing a collapsible chamber on a collecting basin;

positioning an inlet of the collecting basin about a urethral opening of the human female;

ensuring that the collapsible chamber remains compressed while said inlet is positioned about the urethral opening during urination by the human female; and drawing in urine from said collecting basin through a narrowed opening into the collapsible chamber by releasing compression force on said collapsible chamber to permit said collapsible chamber to expand.

\* \* \* \* \*